United States Patent
Alt

[11] Patent Number: 5,824,045
[45] Date of Patent: Oct. 20, 1998

[54] VASCULAR AND ENDOLUMINAL STENTS

[75] Inventor: Eckhard Alt, Ottobrunn, Germany

[73] Assignee: Inflow Dynamics Inc., Arlington, Va.

[21] Appl. No.: 733,553

[22] Filed: Oct. 21, 1996

[51] Int. Cl.$^6$ ........................................................ A61F 2/06
[52] U.S. Cl. ................................ 623/1; 606/191; 623/12
[58] Field of Search ...................................... 606/191, 194, 606/195, 198; 623/1, 12

[56] References Cited

U.S. PATENT DOCUMENTS

| | | | |
|---|---|---|---|
| 5,607,442 | 3/1997 | Fischell et al. | ........................... 606/191 |
| 5,607,463 | 3/1997 | Schwartz et al. | ............................. 623/1 |

*Primary Examiner*—Michael Powell Buiz
*Assistant Examiner*—David O. Reip

[57] ABSTRACT

A vascular or endoluminal stent is adapted for deployment in a vessel or tract of a patient to maintain an open lumen therein. The stent includes a biocompatible metal hollow tube having a multiplicity of openings through an open-ended tubular wall thereof, the tube constituting a single member from which the entire stent is fabricated, and a thin, tightly adherent layer of gold overlying the entire exposed surface area of the tube including edges of the openings as well as exterior and interior surfaces and ends of the wall. The layer may include at least a trace of another noble metal to improve the adherence of the layer to the underlying metal surface of the tube. Plural tightly bonded films superposed one atop another may be used to form a composite layer, but in any event the overall layer has a thickness in a range from approximately 1 micron to approximately 20 microns. The gold coating serves to reduce thrombogenicity, enhance fluoroscopic visibility, and reduce allergic reaction relative to that experienced with implantation of stainless steel and other metal stents in the human body.

17 Claims, 1 Drawing Sheet

VASCULAR AND ENDOLUMINAL STENTS

BACKGROUND OF THE INVENTION

The present invention relates generally to stents which are implantable or deployable in a vessel or duct within the body of a patient to maintain the lumen of the duct or vessel open, and more particularly to improvements in stent structures and in methods for making improved stents.

Stents are expandable vascular and endoluminal prostheses employed to maintain a narrow duct of the human body open and unoccluded, such as a portion of the lumen of a blood vessel—typically, a coronary or femoral artery—following treatment by dilatation of the vessel through balloon catheter angioplasty. Other ducts or tracts of the human body in which a stent might be installed to maintain an open lumen include the tracheo-bronchial system, the biliary hepatic system, the esophageal bowel system, and the urinary tract system. The vascular stent must possess sufficient mechanical strength that offers dimensional stability to resist the inevitable recoil of a blood vessel's elastic wall in response to the distension of the wall during balloon deployment of the stent at a target site in the vessel.

Regardless of the type of stent used—the round wire configured in a zig-zag form as disclosed in U.S. Pat. No. 4,580,568, or the Palmaz-Schatz stent constituting a longitudinal tubular element with a pattern of confluent intersecting struts formed from rectangularly shaped longitudinally oriented openings in its wall as disclosed in European Patent EP 81-0221570, or the Alt et al. stent comprising a smooth tubular composition of repeating longitudinally-displaced sinusoidal waveforms as disclosed in co-pending U.S. patent application Ser. No. 08/599,880 ("the '880 application") which is assigned to the same assignee as this application—certain problems remain to be resolved, although they appear to be present to a considerably lesser extent with a stent of the type described in the '880 application.

Whenever a blood vessel wall is subjected to trauma—as its inner surface is, for example, by the mere implantation of a stent—it undergoes a repair response of intimal hyperplasia, a rapid proliferation of smooth muscle cells in the traumatized region of the wall's surface. The trauma is greater as a consequence of an angioplasty procedure, with the resulting hyperplasia contributing to restenosis and re-occlusion of the vessel lumen in a significant number (about 35%) of patients who have been subjected to the treatment. Typically, the re-emergence takes place within a period of from three to six months following the initial procedure. Repeating the angioplasty procedure is in and of itself largely ineffective as more than an acute solution for this new source of occlusion, compared to the original stenosis attributable to fatty deposits and plaque. The profusion of smooth muscle cell tissue is not readily compressed in any permanent way as was the original source.

The installation of a stent at the angioplasty site, as is now commonly performed, assists in maintaining the lumen of the vessel open. But the stent itself, to a larger or smaller degree, acts as a site for formation of thrombus with the flow of blood through the artery, which further acts to clog the openings in the stent and to accelerate the re-occlusion of the artery. The structure and configuration of the Alt et al stent of the '880 application represent an improvement in that regard as well as for ease of implantation and attainment of symmetrical deployment. The presence of that stent's very smooth, polished surface tends to trap or retain fewer thrombi and lessens the likelihood of severe clotting at the site of the stent. Substantial additional improvement in resisting thrombosis and coagulation is attained by the use of biomaterial coatings of the type disclosed in co-pending U.S. patent application Ser. No. 08/278,806 ("the '806 application") which is also assigned to the same assignee as the present application.

Another factor affecting the decision to implant a stent is the ability of the patient to tolerate the presence of the material of which the stent is composed. Here again, biomaterial coatings can be helpful. But a statistically significant five percent of the patient population is allergic to materials of which currently available stents are composed, including chrome, nickel, and/or medical grade implantable 316L stainless steel, which contains about 20% nickel. In such patients, stent implants are contraindicated and may be used only for acute relief on an emergency basis. Indeed, restenosis can commence within only one or two days to very quickly eliminate the initial benefit enjoyed from implantation of a conventional stent.

It is essential, during the insertion and deployment of a stent, that the progress of advancement of the stent (typically on a balloon catheter) be observable by the implanting physician by means of X-ray fluoroscopy, so that reasonable, albeit limited steps may be taken to traverse partial obstructions in the path of the stent and allow it to be deployed accurately at the desired target site. This generally requires that the wall of the stent be of sufficient thickness to not only withstand the aforementioned vessel wall recoil phenomenon, but to enable it to be seen on the fluoroscope.

Several materials possess the mechanical strength which is suitable for use in a stent structure, one which is particularly effective being 316L stainless steel. Typical stent wall or wire thicknesses range from 70 to 200 microns ($\mu$). A 70 to 80$\mu$ thick 316L steel stent, clearly at the lower end of this range, has been found to provide sufficient strength to resist recoil and to maintain a lumen diameter very nearly corresponding to that achieved by the balloon inflation. But this relatively thin and tiny metal structure creates little shadow on a fluoroscopic picture, since the X-ray absorption of the metal is low. On the other hand, a need for greater wall thickness to enhance radiopacity must be balanced against an increased stent diameter which makes passage through narrow vessels more difficult and risky, as well against a requirement of sufficient radial force to be applied by balloon inflation on the interior surface of the stent during deployment, with concomitant increased risk of balloon rupture.

It is a principal aim of the present invention to provide a stent and method of manufacture thereof which enables optimum mechanical support of the vessel despite a thin stent diameter and low profile, and yet also offers an optimum fluoroscopic appearance so that the position of the stent within the vascular system is readily identified.

Another aim of the invention is to provide such a stent which possesses further properties and characteristics to deter restenosis even without biomaterial coatings, as well as avoid allergic reaction of the patient to the presence of the implanted stent.

SUMMARY OF THE INVENTION

According to the invention, a vascular or endoluminal stent is covered with a very thin, highly adherent layer of gold or other noble metal, such as platinum, or an alloy which is primarily gold or other noble metal with a considerably smaller percentage of a compatible metal which may or may not be another noble metal. Preferably, the noble metal layer is ultra-thin and covers the entire stent—interior as well as exterior surfaces and all edges bounding the internal openings in the wall and the ends thereof if the stent is of the hollow, open-ended tube type, or the entire surface of the wire if the stent is of the zig-zag wire type. The layer is applied in a way to assure that it will adhere tightly to the underlying metal of the stent—typically, medical grade implantable 316L stainless steel—so as to resist peeling or flaking of the layer during insertion, and especially during expansion of the diameter of the stent as it is being deployed in final position in the artery at the target site.

Gold is non-irritating and substantially non-allergenic, so a gold-plated stent may be implanted in patients that even have severe materials allergies. Moreover, it offers a substantially radiopaque surface that enables the stent to be observed without any difficulty as it is being advanced through the vessel lumen to the desired site of deployment. Since it offers high fluoroscopic visibility in a very thin layer, the presence of the gold film allows the thickness of the stent wall to be determined almost solely by considerations of mechanical strength, with consequent reduction of stent external diameter over what would be required if enhanced radiopacity of the base metal were an overriding factor. Finally, but by no means of lesser importance, the gold layer offers a surface of substantially non-thrombogenic characteristics, and therefore reduces the likelihood of an acute closure of the vessel in which it is implanted. And if an acute closure is avoided, it is much more likely that the lumen will kept more permanently open in the region occupied by the stent. The applicant's studies have indicated that the surface charge of gold compared to that of steel leads to only about 40% or less thrombus formation on a gold-coated stent relative to that encountered with uncoated metal stents.

The disadvantage of reduced mechanical strength of noble metals such as gold or platinum—which makes them unsuitable alone for application in the human vascular system—is overcome by the use of a core composed of a material, such as stainless steel, having considerably better mechanical properties than the noble metal. On the other hand, the noble metals have the advantage of from four to six times greater radiopacity than steel, as well as those properties mentioned immediately above. A $10\mu$ layer of gold, for example, has the same shadow density under fluoroscopy as a thickness of 50 to $60\mu$ of steel, thus allowing an overall reduced diameter of the gold-over-steel core compared to a solid steel stent, given the constraint of a fixed minimum internal diameter, which makes it easier for the stent to negotiate the narrow passageway of the vessel during insertion, particularly where the stent is to be implanted in a coronary artery.

Therefore, a more specific aim and objective of the invention is to provide a stent with a thin, tightly adherent, noble metal layer, plate, coat, or covering, preferably of gold, over all exposed surfaces of the stent, to provide the several advantages described in this summary.

Care should be exercised, however, to avoid use of a material for the exterior layer or the entire stent which is of such high fluoroscopic visibility, such as tantalum, that its bold shadow would shield from view a subsequent restenosis within the region of the vessel lumen occupied by the stent.

The principles of the invention are to be distinguished from prior art disclosure of the use of gold as a marker on medical balloons and stents, where application of the gold marker is only over a very limited area that will allow identification of only that certain part of the stent. Such limited use also does not enjoy the advantages offered by the present invention of non-allergenic, non-thrombogenic properties, and reduced diameter and extended visibility of the overall stent. A complicating factor is the stress and strain created on the gold layer as the stent undergoes considerable changes in physical configuration, that can cause fracture, fissuring, cracking, and peeling of the layer. Initially, the stent is crimped onto the balloon so that the inner diameter of the stent is only about 0.6 to 0.7 millimeters (mm), whereas during balloon inflation and after stent deployment at the targeted site in the vessel, the stent inner diameter may be up to about 6 mm. This is not of great concern where gold is applied to only a very tiny surface area, but is a major consideration where the entire expanse of surface area of the stent is to be coated. In the latter case, tight coverage is essential throughout.

According to a preferred method of the invention, a firm and yet lineally extensible bond between the base metal of the stent core or carrier and the noble metal of the outer layer is obtained by a technique of ion beam deposition which is in and of itself a conventional process. For gold, an initial layer is achieved by vaporizing the gold in a vacuum chamber and then accelerating the gold ions onto and in adherent relationship with the surface of the underlying metal, with stable anchoring thereto, to a thickness of $1\mu$ or more. This is preferably followed by a galvanic process to provide a relatively uniform, overall layer thickness of from about 3 to about $6\mu$ including the initial foundation layer.

BRIEF DESCRIPTION OF THE DRAWINGS

The above and still further aims, objects, features, aspects and attendant advantages of the present invention will become apparent from the following detailed description of a preferred embodiment and process of manufacture thereof constituting the best mode presently contemplated of practicing the invention, when taken in conjunction with the accompanying drawings, in which.

DETAILED DESCRIPTION OF A PREFERRED EMBODIMENT AND METHOD

Figure 1A:
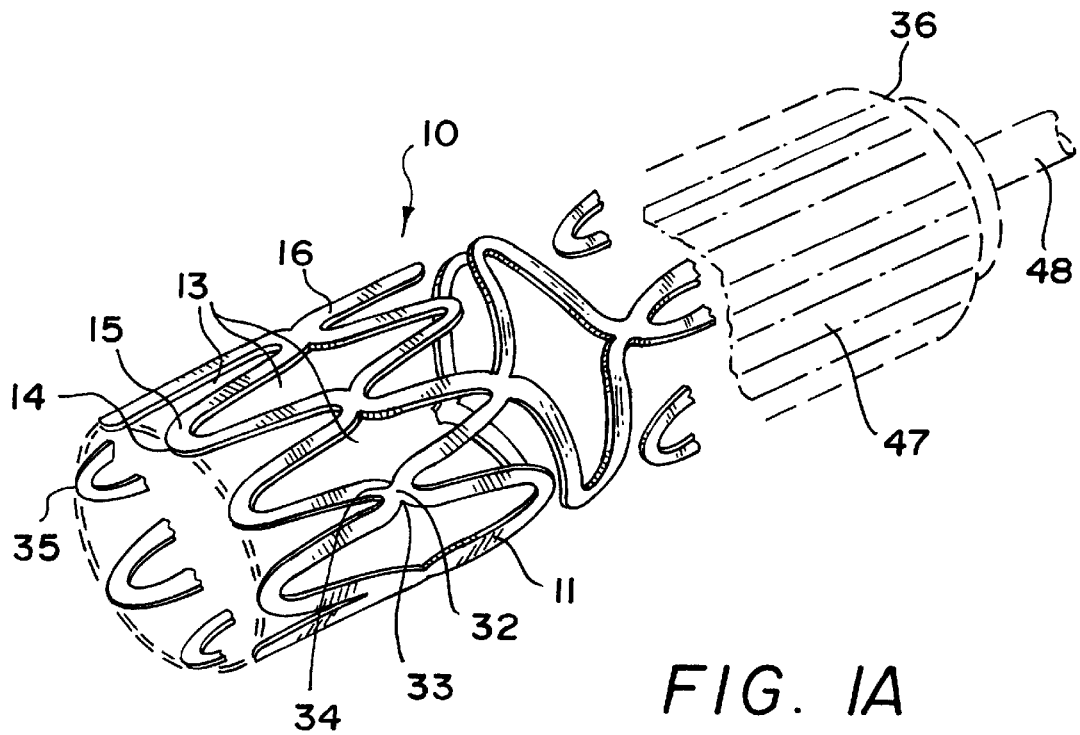
FIGS. 1A and 1B are a fragmentary view, in perspective, of a preferred embodiment of a vascular or endoluminal stent with thin gold plating over its entire surface according to the present invention, and an enlarged detail thereof, respectively.

A stent 10 shown in FIG. 1A (not to scale) is designed and fabricated in a manner preferably corresponding to the Alt et al stent disclosed in the '880 application, which is incorporated in its entirety into this specification by reference. As illustrated, the stent is constructed from a hollow tubular structure or member 11 composed of a biocompatible metal such as medical grade 316L stainless steel, although other metals may alternatively be used, such as titanium or iridium. The tubular member is provided with a multiplicity of openings 13 through its wall 14 which define the stent configuration. Preferably, the openings 13 are precisely cut, for example, within a tolerance of 2 to 3 microns, by a narrow laser beam, on the order of 35 microns ($\mu$) or less.

The biocompatible hollow open-ended tube 11 is the basic member from which the entire stent is fabricated, and the configuration defined by the multiplicity of openings 13 through the wall preferably comprises a plurality of serpentine elements 15, 16, . . . , in the wall that run circumferentially in juxtaposed substantially sine wave-like or sinusoidal patterns. These patterns have a uniform number of multiple cycles, with adjacent ones of the serpentines (e.g., 15, 16) being offset from one another about the circumference of the tubular wall 14.

Each of the interconnecting points, such as 32 between serpentines 15 and 16, includes circumferential notches such as 33 and 34 at either side of the respective interconnection to enhance crimping and symmetric expansion of the stent on a balloon, or means otherwise adapted to exert relatively uniform radial outwardly-directed forces from within the tube. Each of the serpentine elements has a rounded cross-section, preferably oval. The openings 13 have sizes in a ratio of length to width that may range from 4:1 to 10:1, for example. The length of each opening 13 preferably ranges from about 2.0 to about 4.0 millimeters (mm), and the width from about 200$\mu$ to about 300$\mu$. Each serpentine rib (e.g., 16) has a width preferably ranging from about 120$\mu$ to about 240$\mu$, and a thickness ranging from about 65$\mu$ to about 100$\mu$ depending on the specific point along the length of the stent at which the measurement is taken. In that respect, the thickness of the tube wall may be varied from the longitudinal middle of the tube to each end, to provide end portions of tapering outer diameter. Alternatively, the wall may be of uniform thickness throughout. The ends 35, 36 themselves of tube 11 are series of undulations in the sine wave-like pattern of the serpentine occupying that respective segment in the basic stent structure.

The stent is preferably pre-opened after fabrication to relieve stresses. For a starting diameter of 1.6 mm, the pre-opened diameter may at the lower end of a range from 2.0 to 2.3 mm. Pre-opening produces a stent inner diameter that allows the stent to slide comfortably over the uninflated balloon, for crimping it onto the balloon.

At this point in the overall stent fabrication process annealing is performed by heating the serpentine structure to a temperature that depends on the material from which the original tube was produced, for a predetermined interval of time. The pre-opened stent as annealed is to be delivered for implantation by the physician, or the completed stent 10 may be pre-mounted on a balloon 47 (shown in fragmentary phantom form) of a catheter body 48 and delivered in a sterile package as a complete assembly ready for use by the physician, so that the device need only be unpackaged and implanted.

Figure 1B:
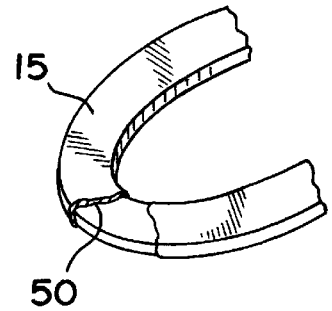

According to the present invention, however, before or after the pre-opening and annealing steps, the stent is coated with a thin, tightly adherent layer 50 (FIG. 1B, shown partly in section for clarity) of noble metal, preferably gold, but alternatively an alloy which is primarily composed of gold with a substantially lesser percentage of silver or other noble metal, or a different single noble metal or metal alloy of similar properties. The noble metal layer is applied to cover the entire exposed surface of the basic metal stent, whether it be of the tubular type as has been described, or a metal mesh of zig-zag form, or other configuration. Preferably, the layer has a thickness in the range from approximately 1$\mu$ to approximately 20$\mu$, and more preferably about five $\mu$.

Figure 2:
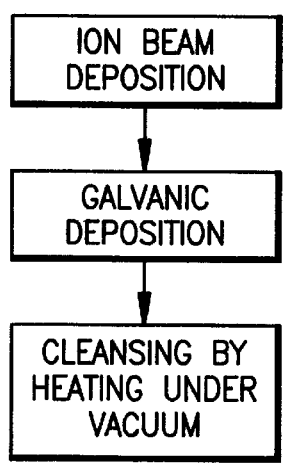
FIG. 2 is a flow chart of an exemplary simplified process for producing the overall thin adherent gold layer on a stent according to the invention.

The thin, adherent film or layer 50 of gold of suitable characteristics may be provided, for example, by means of one or more conventional processes, a simplified flow diagram for which is shown in FIG. 2. Preferably the process commences with ion beam deposition of gold onto the surface of the core or base metal to provide a firm, tightly bonded, extremely thin foundation layer, but one which allows the bond between base metal and noble metal to flex without suffering fracture or peeling of the overlying layer.

Gold ions from vaporized gold are accelerated in a vacuum environment to deposit on the exposed surfaces of the metal core of the stent. Preferably, this initial foundation layer is built upon by then employing a conventional galvanic process to apply one or more additional thin, tightly adherent uniform layers of gold onto the foundation layer or intervening layer as the case may be, to form an overall composite layer of gold having a thickness of from about 3$\mu$ to about 6$\mu$. For this portion of the process, for example, a stainless steel stent is used as one of a pair of electrodes submerged in an electrolytic bath of appropriate solution of gold constituency. A voltage is applied across the electrodes to establish a current of sufficient magnitude to form one or more thin electroplate layers of gold on the stent. The overall effect of these processes is to provide the adherence that will preclude cracking, peeling or flaking of any portion of the overall gold layer from the underlying surface of the steel core, which would otherwise tend to occur during times when the stent is undergoing mechanical stress and distortion, such as during the pre-opening, crimping, and expansion-during-deployment phases of the procedure.

To eliminate the presence of impurities that may be attracted to the surface of the gold as a consequence of the overall deposition process or thereafter, the coated stent is preferably subjected to a cleansing step by heating under vacuum to a temperature which will depend upon the nature of the coating and the underlying material. In the case of gold on steel, for example, the cleansing step may be carried out at a temperature of about 250° Celsius and a pressure of about 0.10 atmosphere. It is possible that the annealing step referred to earlier may be carried out as part of the cleansing step where that portion of the process is performed after the gold coating has been applied.

Although a tubular metal element has been described, the principles of the invention may be applied to any known type of stent, by covering its entire surface with the noble metal layer. The advantages of such a full layer on the surface of the stent have been discussed in the invention summary above. Also, although gold is the preferred noble metal for the overlying layer on the stent, other radiopaque materials of similar properties, such as platinum, or alloys of gold or platinum with other noble metals, such as small amounts of silver, could alternatively be employed subject to the considerations noted herein.

Whether pre-mounted by crimping onto a balloon, or subsequently mounted on the balloon at the time it is to be installed in the patient, the crimped stent should have an outer diameter in a range from about 0.9 to about 1.2 mm, and inner diameter in a range from about 0.6 to about 0.7 mm. When fully deployed in the patient's blood vessel at the target site by inflation of the expansion balloon, the stent's inner diameter will typically lie in a range from about 2.5 to about 5.0 mm, with a maximum of about 6.0 mm. Final deployed diameter, of course, must be adequate to assure retention of the stent in the vessel in firm contact with the vessel wall (and, if desired, even partly imbedded in the vessel wall to present a relatively smooth continuous lumen to lessen the possibility of blood flow turbulence).

The dimensions of the serpentines and of the openings between them in the tubular wall of the stent, as well as the characteristics of the balloon, will ultimately determine the minimum diameter to which the stent may be crimped on the balloon—typically, 1.0 mm—and the maximum diameter to which the stent may be dilated by the balloon during deployment—typically, 6.0 mm (inner diameter).

The stent may be produced in lengths ranging from about 5.0 to about 25.0 mm. But stents of the various prior art types are typically supplied in two standard lengths, one of which is toward the lower end of the range (e.g., a length of about 8.0 to about 9.5 mm) and the other in the mid to higher end (e.g., a length of about 15.0 mm), because the expansion balloons for deploying the stents are customarily available in a length of either about 10 mm or about 20 mm. Other stent lengths are available on a custom basis, but occasionally it is necessary to implant two stents actually or virtually abutting each other when the length of the injured tissue at the target site is greater than accommodated by a single available length, or because the stent length is limited by a need for sufficient flexibility to be advanced through the vascular system to the target site.

From the foregoing, it will be appreciated that an improved stent structure and method for making the same have been disclosed that provides not only enhanced visibility while attaining diameters sufficiently small to facilitate ease of advancement of the stent through tortuous, narrowed vessels, but also reduces thrombogenicity and allergic responses to stent implantation among the patient population.

Although certain preferred embodiments and methods have been disclosed herein, it will be appreciated by those skilled in the art to which the invention pertains, from a consideration of the foregoing description, that variations and modifications may be made without departing from the spirit and scope of the invention. Accordingly, it is intended that the invention shall be limited only by the appended claims and the rules and principles of applicable law.

What is claimed is:

1. A vascular or endoluminal stent adapted for deployment in a vessel or tract of a patient to maintain an open lumen therein, comprising:

a biocompatible metal hollow tube having a multiplicity of openings through an open-ended tubular wall thereof, said tube constituting a single member from which the entire stent is fabricated and having a predetermined inner diameter in a production state and adapted to be expanded to a larger diameter for deployment in said vessel or tract, and a thin, tightly adherent coating of gold of substantially uniform thickness and density overlying the entire exposed surface area of the tube including edges of said openings as well as exterior and interior surfaces and ends of said wall, said gold coating being composed of plural tightly bonded layers superposed atop one another.

2. The stent of claim 1, wherein the gold coating includes at least a trace of another noble metal to improve the adherence of the foundation layer in physical contact with said exposed surface area to the underlying metal surface of the tube.

3. The stent of claim 1, wherein the gold coating has a thickness in a range from approximately 1 micron to approximately 20 microns.

4. The stent of claim 3, wherein the gold coating has a thickness of approximately 5 microns.

5. A vascular or endoluminal stent adapted for deployment in a vessel or tract of a patient to maintain an open lumen therein, comprising:

a generally cylindrical open-ended biocompatible metal element having a multiplicity of radial through-holes therein, and a thin, substantially uniform noble metal coating over the entire exposed surface of the cylindrical element including the edges of the through-holes as well as interior and exterior surfaces and ends of the cylindrical element and forming a tight bond therewith resistant to rupture while undergoing radial expansion and longitudinal contraction of the cylindrical element during deployment of the stent, said noble metal coating including at least two homogeneous layers, the layer residing directly upon the surface of the cylindrical element being a foundation layer deposited by a process to enhance adhesion thereto.

6. The stent of claim 5, wherein said noble metal coating is composed primarily of gold.

7. The stent of claim 5, wherein the foundation layer of said noble metal coating is an ion beam deposition.

8. The stent of claim 7, wherein the number of said homogeneous layers is two, and the layer of said noble metal coating atop said foundation layer is an electroplate.

9. The stent of claim 5, wherein said metal element is a wire mesh.

10. The stent of claim 5, wherein said metal element is a hollow tube.

11. A method of fabricating a vascular or endoluminal stent adapted for deployment in a vessel or tract of a patient to maintain an open lumen therein, comprising the steps of:

forming an open-ended tubular biocompatible metal element with through-holes in the wall thereof sufficient in size and number to enable radial expansion of the element, coating the entire surface of the tubular metal element including exterior and interior surfaces and ends of said wall and edges of said through-holes therein with a thin, tightly adherent coat of substantially uniform thickness of noble metal, wherein said coating step includes the steps of vapor depositing a first foundation layer onto the entire surface of said element, followed by galvanically depositing a second layer onto the entire exposed surface of said first foundation layer.

12. The method of claim 11, wherein the step of coating comprises depositing the noble metal over said entire surface of the tubular metal element to a thickness in a range from 1 to 20 microns.

13. The method of claim 12, wherein the step of galvanically depositing produces a thickness of said noble metal coat in a range of from 3 to 6 microns.

14. The method of claim 12, wherein the noble metal is gold.

15. The method of claim 12, wherein the noble metal is gold alloy.

16. A method of fabricating a vascular or endoluminal stent adapted for deployment in a vessel or tract of a patient to maintain an open lumen therein, comprising the step of forming an open-ended tubular biocompatible metal element with through-holes in the wall thereof, and coating the entire surface of the tubular metal element including exterior and interior surfaces and ends of said wall and edges of said through-holes therein with a thin, tightly adherent layer of noble metal, wherein the step of coating comprises depositing the noble metal over said entire surface of the tubular metal element to a thickness in a range from 1 to 20 microns, and including pre-opening the stent either before or after applying the noble metal coating.

17. A stent for insertion into and placement at a target site in a vessel of a patient for maintaining the lumen of said vessel open, comprising:

a tubular, thin-walled, open-ended metal structure having a multiplicity of through-holes in the side wall thereof to allow radial expansion upon exertion of pressure on the side wall from within the lumen of the stent for placement at said target site in the vessel, and a thin coating of at least one noble metal of substantially uniform thickness overlying the entire exposed surface of the tubular structure including the interior and exterior surfaces and the edges of the through-holes and end surfaces thereof, said coating composed of two separate contiguous overlying layers, a first of said layers residing against and in adherent relation to said entire exposed surface of the tubular structure, and the second of said layers bonded to the first layer and combining therewith to resist rupture of said coating during radial expansion of said tubular structure.

* * * * *